(12) United States Patent
Shimozato (10) Patent No.: US 9,326,681 B2
(45) Date of Patent: May 3, 2016

(54) NON-CONTACT TONOMETER, CONTROL METHOD OF THE SAME, AND PROGRAM

(71) Applicant: CANON KABUSHIKI KAISHA, Tokyo (JP)

(72) Inventor: Yuki Shimozato, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 100 days.

(21) Appl. No.: 14/246,430

(22) Filed: Apr. 7, 2014

(65) Prior Publication Data

US 2014/0316232 A1 Oct. 23, 2014

(30) Foreign Application Priority Data

Apr. 17, 2013 (JP) ................................. 2013-086791

(51) Int. Cl.
*A61B 5/00* (2006.01)
*A61B 3/16* (2006.01)

(52) U.S. Cl.
CPC ...................... *A61B 3/165* (2013.01)

(58) Field of Classification Search
CPC ...................................... A61B 3/165
USPC ............................... 600/398–401
See application file for complete search history.

(56) References Cited

U.S. PATENT DOCUMENTS 5,299,573 A * 4/1994 Kobayashi ............. A61B 3/165
600/401
2014/0257076 A1* 9/2014 Shimozato

FOREIGN PATENT DOCUMENTS

JP 06-007306 A 1/1994
JP 07-100116 A 4/1995
JP 08-000109 B2 1/1996

* cited by examiner

*Primary Examiner* — Brian Szmal
(74) *Attorney, Agent, or Firm* — Fitzpatrick, Cella, Harper & Scinto (57) ABSTRACT

An excessive amount of pressurized air is inhibited from being blown to an eye of a patient during measurement of a corneal shape deformation amount. In a non-contact tonometer having a piston, a driving unit to drive the piston, a fluid ejection unit to blow air pressurized by driving the piston toward a cornea of an eye to be inspected, and an intraocular pressure measuring unit to detect a deformed state of the cornea and measure an intraocular pressure, there are provided a piston displacement restricting unit that restricts a displacement amount when the piston pressurizes the air, and a changing unit to change the displacement amount to be restricted by the piston displacement restricting unit.

9 Claims, 9 Drawing Sheets

NON-CONTACT TONOMETER, CONTROL METHOD OF THE SAME, AND PROGRAM

BACKGROUND OF THE INVENTION

1. Field of the Invention

The present invention relates to a non-contact tonometer that calculates an intraocular pressure value from a corneal shape deformation detection signal when air is blown to an eye to be inspected, a control method of the same, and a program to execute the control method.

2. Description of the Related Art

Many of non-contact tonometers have constitution where a piston pushes air in a cylinder outwardly, to pressurize the air in an air chamber, and the pressurized air is ejected from a nozzle. For the driving of the piston, a rotary solenoid is usually used because an initial torque of the rotary solenoid is strong and a stroke thereof is long. Furthermore, control is executed to turn off energize to the rotary solenoid on the basis of a corneal shape deformation detection signal, when a cornea is deformed into a predetermined state that is necessary for tonometry. However, even after the energization to the rotary solenoid is turned off, the piston continues to move for a while by an inertia force. Therefore, the air unnecessary for the tonometry is blown to an eye to be inspected, and hence an excessive burden is imposed on a patient. For the purpose of reducing the unnecessary air as much as possible, it is necessary to decrease a movement of the piston by the inertia force.

To decrease the movement of the piston by the inertia force, in Japanese Patent Application Laid-Open No. H08-000109, a method has been suggested in which when it is detected that a cornea is deformed as much as a predetermined amount, the piston is moved backward. Furthermore, in Japanese Patent Application Laid-Open No. H07-100116, a method has been suggested in which when it is detected that the cornea is deformed as much as the predetermined amount, the movement of the piston is decelerated or stopped by using a brake mechanism such as an electromagnetic coil or a disc brake.

In general, a direction of a force to be applied to the piston by the rotary solenoid is an only pressurizing direction of the air. Therefore, it is difficult for the rotary solenoid alone to execute control so that the piston advancing in the pressurizing direction of the air is rapidly decelerated, stopped or moved backward. Therefore, for implementing the above-mentioned prior art, it is necessary to apply the force from the outside to the piston in an opposite direction to the air pressurizing direction, separately disposing a drive mechanism such as the solenoid or a motor as in Japanese Patent Application Laid-Open No. H07-100116. However, a response time of a usual drive mechanism such as the solenoid or the motor is longer than a time from when the cornea starts to be deformed to the end of the blowing of the air. Therefore, even when there is separately disposed the drive mechanism that applies the force of the opposite direction to the piston on the basis of a corneal shape deformation signal, the drive mechanism starts to operate after the blowing of the air weakens or ends. Therefore, in the above-mentioned prior arts, the time required for the control is excessively long, and hence temporally difficult to reduce the air to be blown.

SUMMARY OF THE INVENTION

The present invention to solve the above-mentioned temporal problem and decrease a movement of a piston by inertia. Furthermore, the present invention is to provide a non-contact tonometer that reduces air to be blown and further decreases burdens on a patient, a control method of the same, and a program.

There is provided a non-contact tonometer according to the present invention having a piston, a driving unit to drive the piston, a fluid ejection unit to blow air pressurized by driving the piston toward a cornea of an eye to be inspected, and an intraocular pressure measuring unit to detect a deformed state of the cornea and measure an intraocular pressure, characterized by having a piston displacement restricting unit that restricts, to a predetermined displacement amount, a displacement amount when the piston pressurizes the air.

The piston is not controlled on the basis of a corneal shape deformation signal, but a movement of the piston is beforehand restricted to a predetermined displacement amount, so that air unnecessarily blown to an eye to be inspected can be reduced.

Further features of the present invention will become apparent from the following description of exemplary embodiments with reference to the attached drawings.

DESCRIPTION OF THE EMBODIMENTS

Hereinafter, on embodiment of the present invention will be described in detail with reference to the accompanying drawings.

First Embodiment

Figure 1:
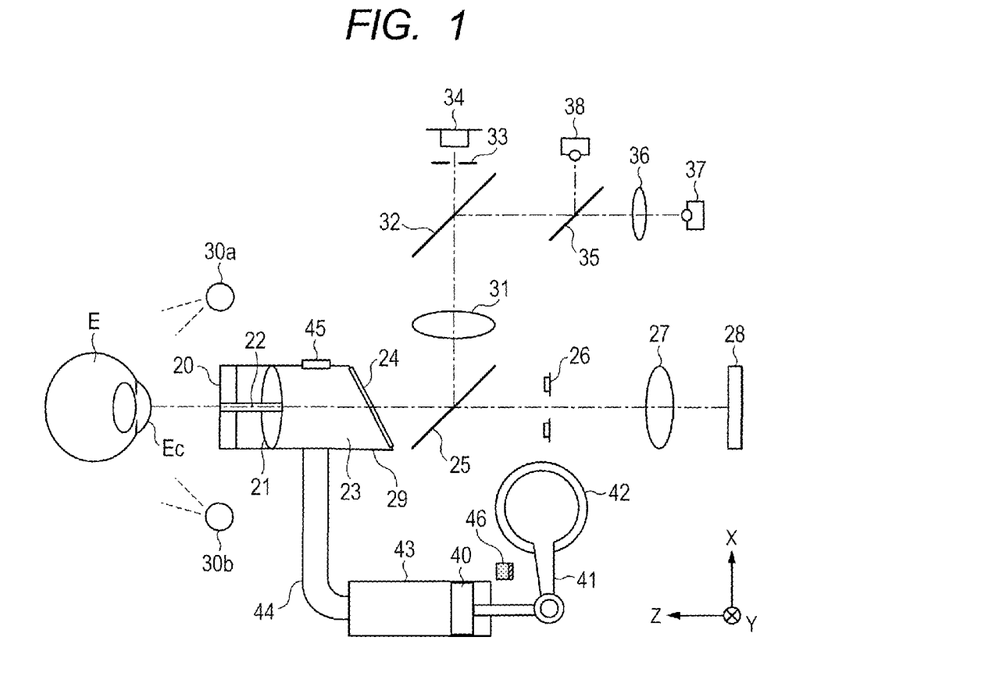
FIG. 1 is a view schematically showing a constitution of a non-contact tonometer in one embodiment of the present invention.

A schematic constitutional view of a non-contact tonometer of a first embodiment of the present invention is shown in FIG. 1.

First, description of an optical system of the present apparatus is made. A measuring light source 37 is a near infrared LED to be used for measurement and also for alignment to an eye E to be inspected. In an emitting direction of the measuring light source 37, a projection lens 36, a half mirror 35 and a half mirror 32 are arranged. In a reflecting direction of the half mirror 35 as seen from the half mirror 32, there is disposed a fixation light source 38 as an LED to be seen by a patient in a fixed manner. In a reflecting direction of the half mirror 32 as seen from the half mirror 35, a relay lens 31 is disposed.

A nozzle 22 is disposed to face a cornea Ec of the eye E to be inspected on a central axis of a parallel flat glass 20 and an objective lens 21. Behind the nozzle, an air chamber 23, an observation window 24, a dichroic mirror 25, a prism diaphragm 26, an image forming lens 27 and an image pickup element 28 are successively arranged. These components constitute a light receiving optical path and an alignment detecting no optical path of an observation optical system for the eye E to be inspected.

The parallel flat glass 20 and the objective lens 21 are supported by an objective barrel 29, and outside the objective barrel, anterior ocular segment illumination light sources the 30a and 30b that illuminate the eye E to be inspected are arranged. It is to be noted that for convenience of explanation, the anterior ocular segment illumination light sources 30a and 30b are shown on the upside and downside of the drawing, but actually the light sources are arranged to face each other is an optical axis vertically to the drawing.

In an incident direction of the half mirror 32 as seen from the relay lens 31, an aperture 33 and a light receiving element 34 are arranged. It is to be denoted that the aperture 33 is disposed at a position where a cornea reflected moo of the measuring light source 37 is conjugated during predetermined deformation, and the aperture constitutes a deformation detection receiving optical system together with the light receiving element 34, when the cornea Ec is deformed in a visual axis direction. The relay lens 31 is designed to form, at a position of the aperture 33, a cornea reflected image of about the same size as in the aperture 33, during the predetermined deformation of the cornea Ec.

Next, description of an air ejection mechanism of the present apparatus will be made. The inside of the air chamber 23 is connected to a pressure sensor 45 that monitors an inner pressure of the air chamber, and a transfer tube 44 that transfers pressurized air from a cylinder 43 into the it chamber. A piston 40 is fitted in the cylinder 43, and the piston 40 is driven by a rotary solenoid 42. A rotary movement of the rotary solenoid 42 is converted into a linear movement of the piston 40 by a driving lever 41 interposed between the rotary solenoid 42 and the piston 40. When the piston 40 moves at a high speed in the cylinder 43, the air in the cylinder 43 is transferred to the air chamber 23 through the transfer tube 44, and the pressurized air passes through the nozzle 22, and is ejected to the eye E to be inspected in this mechanism.

The rotary solenoid 42 and the driving lever 41 are illustrated as one configuration of a driving unit to drive the piston 40 in the present invention, and the constitution including the cylinder 43, the transfer tube 44, the air chamber 23 and the like is illustrated as one configuration of a fluid ejection unit to blow the air pressurized by driving the piston 40 toward the eye to be inspected. Furthermore, to implement the present invention, a stopper 46 is disposed on a range where the driving lever 41 moves, when the piston pressurizes the air. The stopper 46 is illustrated as one configuration of a piston displacement restricting unit to restrict lot a displacement amount when the piston 40 pressurizes the air in the cylinder 43. The piston displacement restricting unit of the configuration does not move from a position where the unit is disposed even when an external force is applied thereto and further, the unit has such a function that in accordance with conditions, the displacement amount of the piston 40 itself is changed in accordance with the position of the unit. It is to be noted that in the present configuration, the stopper 46 is disposed in a movable range of the driving lever 41 as one constitution of the driving unit. However, the present invention is not limited to the configuration, and the piston displacement restricting unit may be any member, as long as the member is disposed in the movable range of at least one of the piston 40 and the one constitution of the driving unit, and finally performs a function of restricting the displacement amount of the piston 40.

Figure 2:
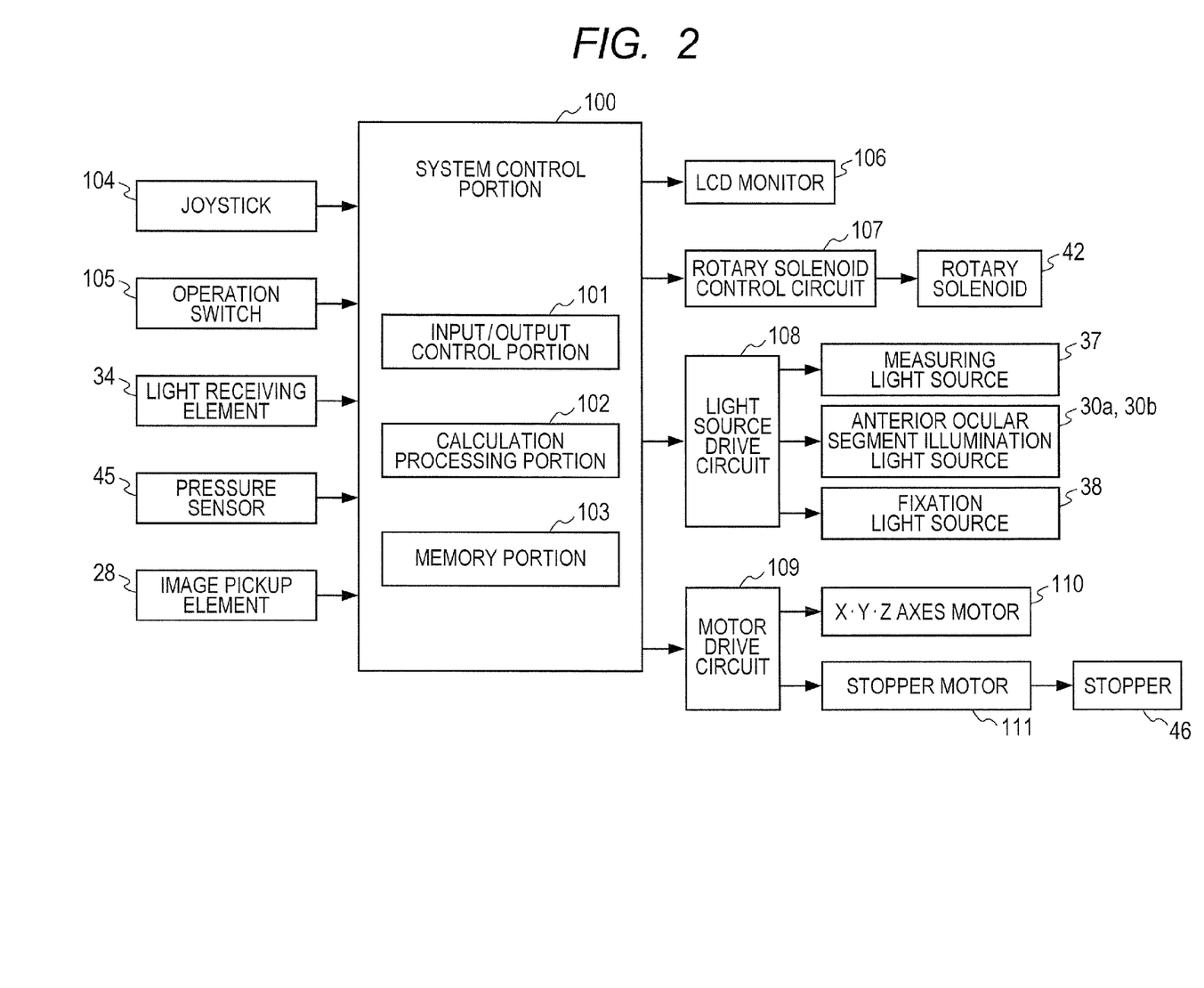
FIG. 2 is a diagram showing a system constitution of the non-contact tonometer in the embodiment shown in FIG. 1.

Next, description of a system constitution of the present apparatus shown in FIG. 2 will be made. A system control portion 100 that controls the whole system has an input/output control portion 101 that controls input and output for various devices, a calculation processing portion 102 that calculates data obtained from the various devices, and a memory portion 103 in which a program, a set value and data obtained by measurement are stored. The system control portion 100 is connected to a joystick 104 that performs the positioning of the optical system to the eye E to be inspected, an operation switch 105 that that performs various operations of the apparatus, for example, the start of the measurement, the light receiving element 34 that receives the cornea reflected image, the pressure sensor 45 that measures the pressure of the air chamber, and the image pickup element 28 that performs observation of an anterior ocular segment image, and signals are input from these components into the system control portion. Furthermore, the system control portion is connected to an LCD monitor 106 that performs screen display, a rotary solenoid control circuit 107 that drives the piston, a light source drive circuit 108 that executes control to turn on or off the above-mentioned various light sources, and a motor drive circuit 109 that performs alignment adjustment of the optical system and the like during the measurement, and position adjustment of the stopper 46, and the system control portion outputs signals to these components.

Figure 3A:
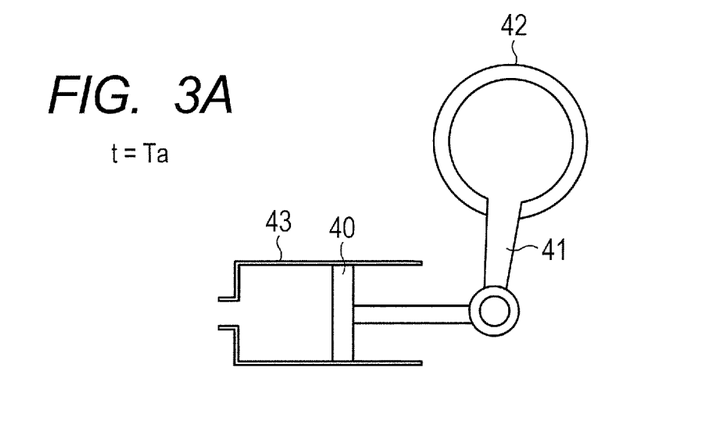
FIGS. 3A, 3B and 3C are explanatory views concerning a piston position in a conventional constitution.
Figure 3B:
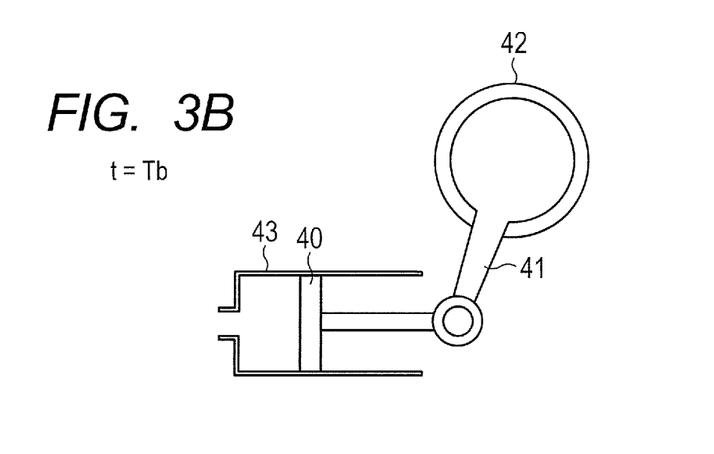
Figure 3C:
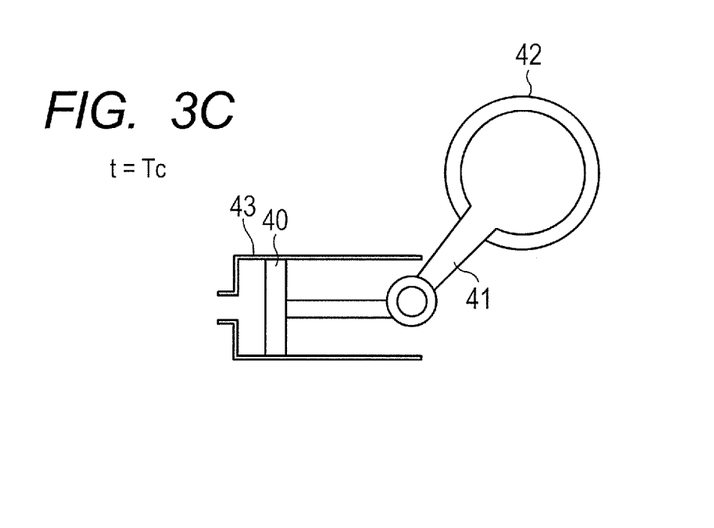
Figure 4:
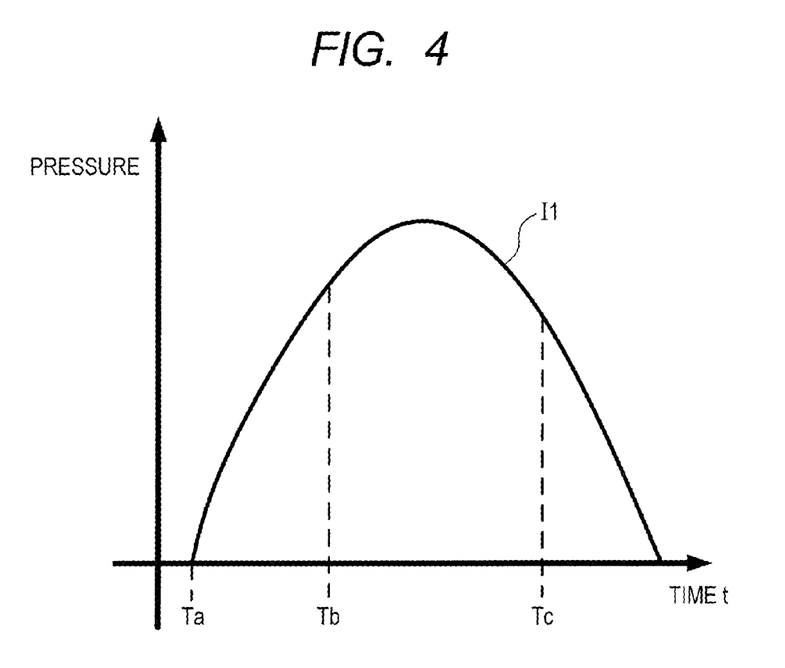
FIG. 4 is a pressure waveform diagram in the conventional constitution.

Here, there are described the movement of the piston and a pressure change of the pressurized air, when an intraocular pressure is measured by a non-contact tonometer of a conventional constitution. FIG. 3A shows a piston position at a time Ta when the piston starts to be driven, FIG. 3B shows a piston position at a time Tb when the cornea is deformed into a state where an intraocular pressure can be measured, and FIG. 3C shows a piston position at a time Tc when the piston is stopped. The pressure change of the pressurized air at this time is shown in FIG. 4. At the time Tb, data necessary for the measurement of the intraocular pressure is obtained, and hence energization to the rotary solenoid is turned off, but after the time Tb, the piston continues to move for a while by an inertia force. Therefore, the piston continues to pressurize the air, and the air unnecessary for the intraocular pressure measurement is blown. It is to be noted that in the above description, the energization to the rotary solenoid 42 is turned off when the cornea is deformed into the state where the intraocular pressure can be measured, but the energization may be turned off at a moment at which a corneal shape deformation signal or a pressure signal is in excess of a predetermined threshold value.

Next, details of the present invention will be described. In general, it is considered that an intraocular pressure value of a healthy eye is from 10 to 20 mmHg, but when the patient has an eye disease such as glaucoma, the patient has a high intraocular pressure of 20 mmHg or more. Therefore, a usual tonometer has a broad measurement range of 0 to about 60 mmHg. To measure the eye of the high intraocular pressure, the air has to be highly pressurized. Therefore, the piston cylinder has a structure where a maximum displacement amount of the piston is excessively long for the displacement amount necessary for the healthy eye. Consequently, during the measurement of the healthy eye, the piston moves as much as the displacement amount necessary for the intraocular pressure measurement, and then continues to move until the inertia force runs out, because a mechanism that intentionally stops the piston is not disposed. Thus, in the present invention, the displacement amount of the piston is determined so that the movement of the piston by the inertia force is decreased. Furthermore, the present invention is characterized in that a member such as the stopper is beforehand disposed to intentionally stop the piston so that the piston moves only as much as the displacement amount thereof.

Figure 5A:
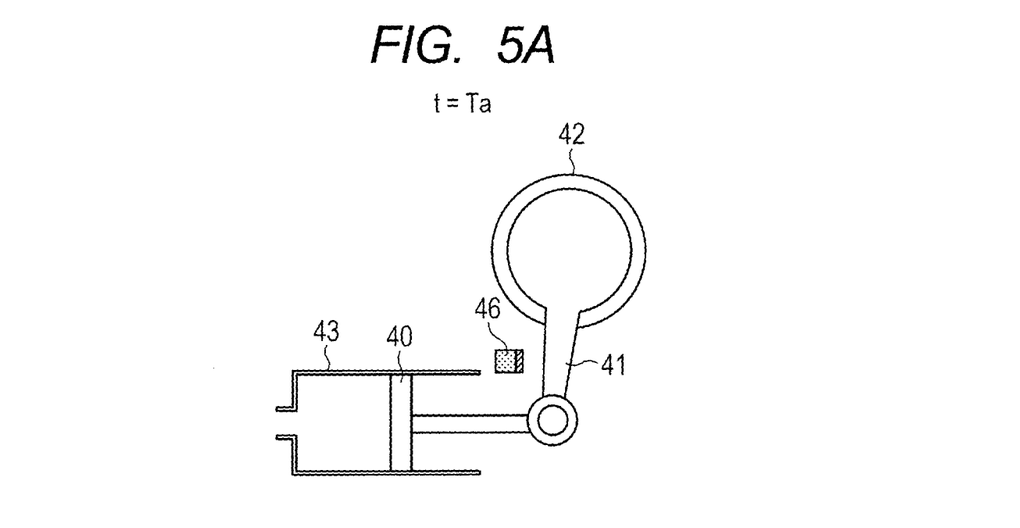
FIGS. 5A and 5B are explanatory views concerning a piston position in the embodiment shown in FIG. 1.
Figure 5B:
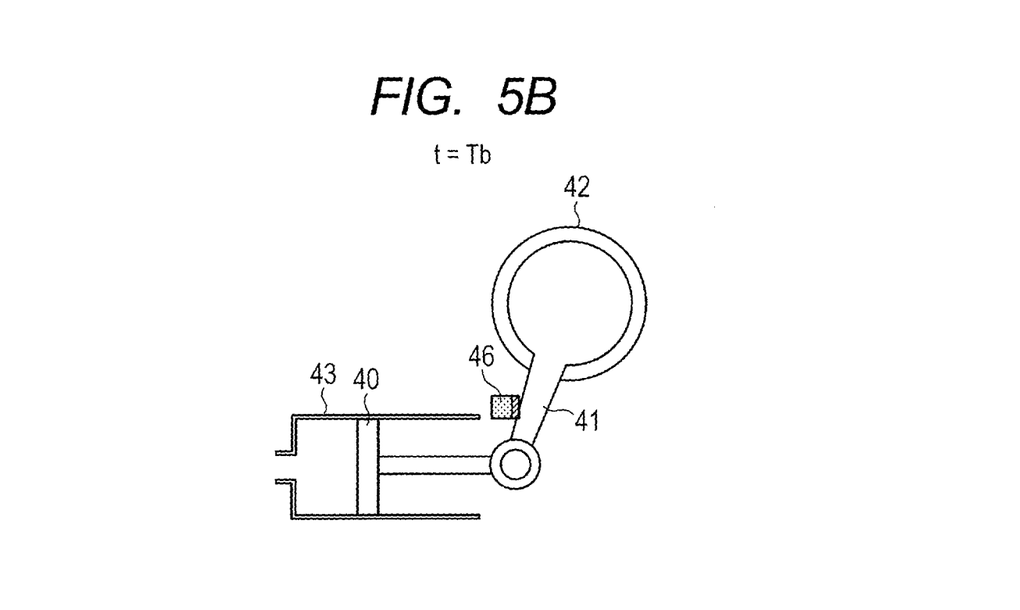
Figure 6:
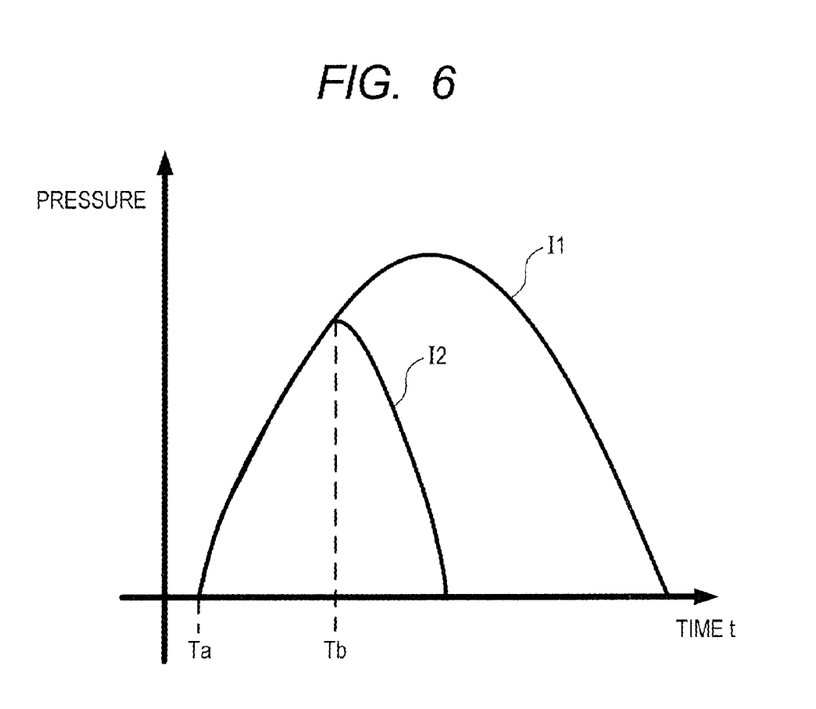
FIG. 6 is a pressure waveform diagram in the embodiment shown in FIG. 1.

There will be described the movement of the piston and the pressure change of the air when the intraocular pressure is measured by the non-contact tonometer of the constitution including the stopper. FIG. 5A shows a piston position at a time Ta when the piston starts to be driven, and FIG. 5B shows a piston position at a time Tb when the cornea is deformed into the state where the intraocular pressure can be measured. The pressure change of the pressurized air at this time is shown in FIG. 6. In FIG. 6, I1 shows the pressure change in the conventional constitution, and I2 shows the pressure change in the constitution of the present invention, respectively. In the present invention, when the piston moves as much as the displacement amount necessary for the intraocular pressure measurement, the piston comes in contact with the stopper immediately after the movement, and then stops. Therefore, as shown by I2 of FIG. 6, the pressure of the air immediately lowers. Consequently, in the constitution of the present invention, the intraocular pressure can be measured similarly to the conventional constitution, and the air to be blown can be reduced.

Figure 7A:
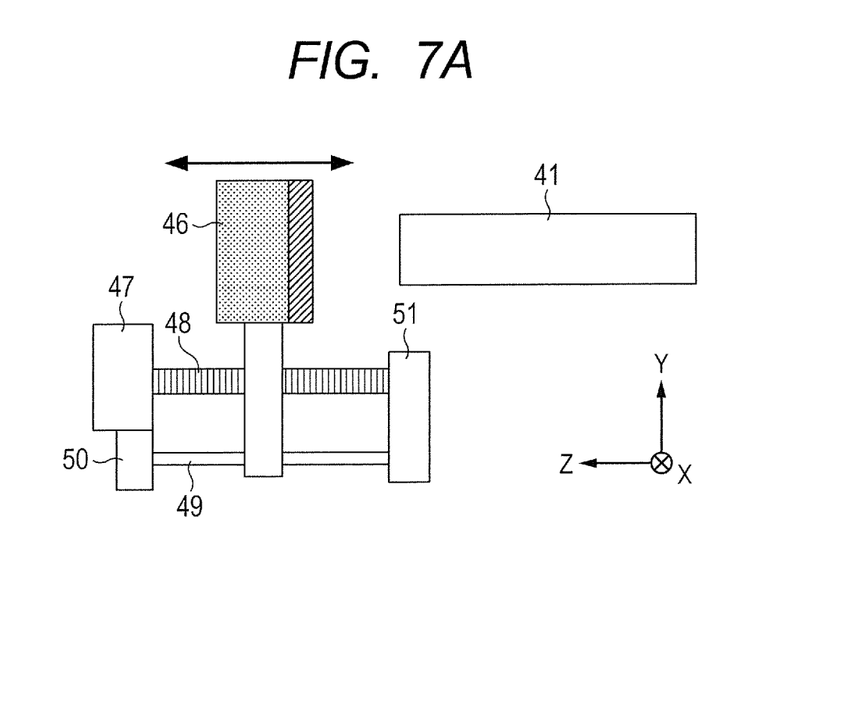
FIGS. 7A and 7B are explanatory views schematically showing a stopper position adjustment mechanism.
Figure 7B:
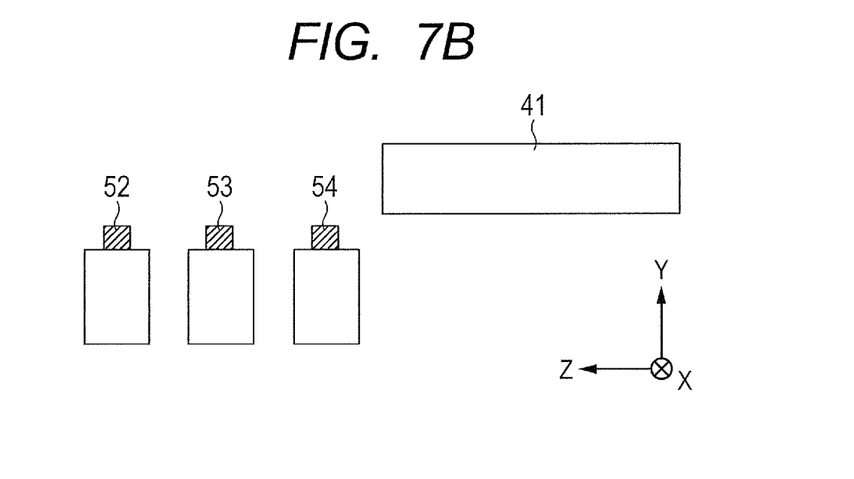

Next, a position where the stopper is disposed will be described. The displacement amount of the piston that is necessary for the measurement varies in accordance with an intraocular pressure value to be measurable. For example, in a case where the eye of a high intraocular pressure is measured, the displacement amount necessary for the measurement is large as compared with a case where the eye of a low intraocular pressure is measured. Therefore, the position of the stopper is adjusted in accordance with a range of the intraocular pressure values that are to be measurable, i.e., the measurement range. As shown in FIG. 7A, the stopper 46 is moved in a Z-axis direction by use of a motor 47 (a constitution 111 in FIG. 2) to adjust a position where the stopper comes in contact with the driving lever 41. Furthermore, as shown in FIG. 7B, rectilinear solenoids 52, 53 and 54 each provided with a stopper projecting in a Y-axis direction may be disposed, and in accordance with the measurement range, one of the solenoids to be driven may be selected so that the stopper comes in contact with the driving lever 41. It is to be noted that FIGS. 7A and 7B are a view showing the vicinity of the stopper 46 and the driving lever 41 of FIG. 1 as seen from an X-axis direction.

Each of these constitutions is illustrated as a part of a changing unit to beforehand change and determine the displacement amount of the piston 40 that is restricted by the piston displacement restricting unit illustrated by the stopper 46. On the basis of the measurement range of the intraocular pressure value measured as described later, in a module region that functions as a part of the changing unit in the system control portion 100, these constitutions are operated to move the arrangement of the stopper 46, thereby changing the displacement amount of the piston 40.

Figure 8A:
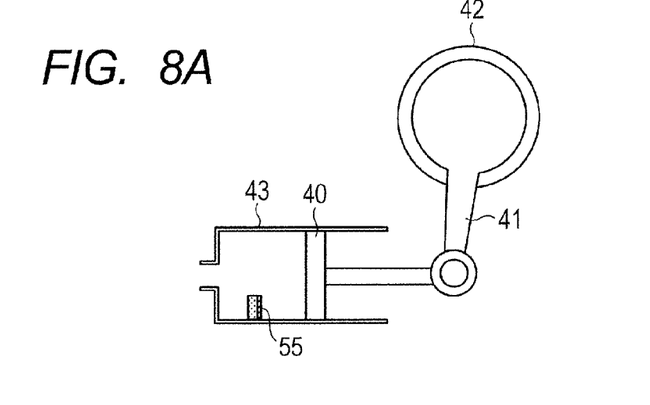
FIGS. 8A, 8B and 8C are explanatory views concerning another configuration of a stopper mechanism.

Furthermore, the constitution of FIG. 1 has mechanism in which the driving lever 41 coupled to the piston comes in contact with the stopper 46 disposed outside the cylinder, to stop the piston. However, as shown in FIG. 8A, a stopper 55 may be disposed in a cylinder so that the piston 40 comes in contact with the stopper 55, to stop the piston.

Figure 8B:
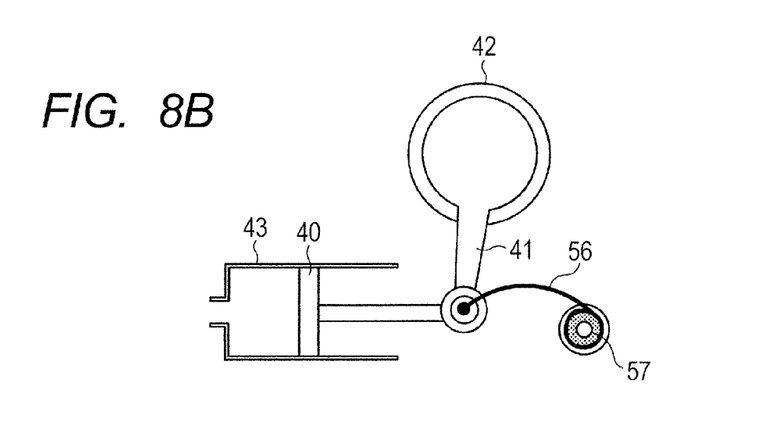
Figure 8C:
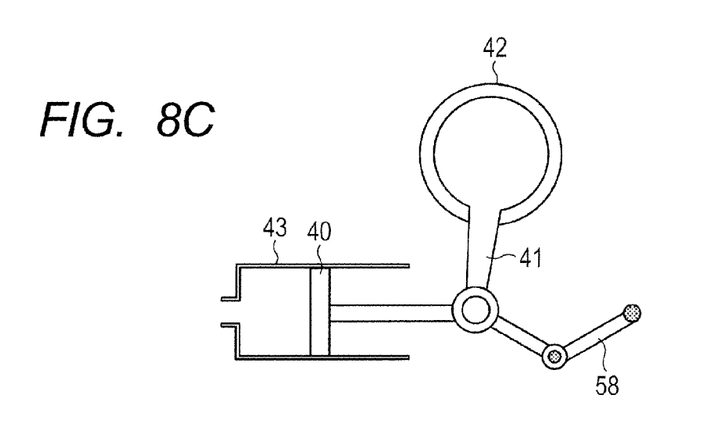

Furthermore, the constitution described up to now is the constitution provided with the mechanism to apply the piston stopping force to the driving lever 41 in a driving direction of the piston, but may be a constitution provided with a mechanism to apply the piston stopping force to the driving lever 41 in a direction opposite to a pressurizing direction of the piston. As shown in FIG. 8B, a band 56 and a reel 57 that winds up the band are disposed, and an end of the band is connected to at least one of the piston 40 and the driving lever 41. When the piston moves as much as the displacement amount necessary for the intraocular pressure measurement or more, the band 56 completely stretches, so that a tensile force of the band 56 is applied to the piston 40, to stop the piston. Examples of a material of the band include chemical fibers, a metal, and a rubber. Furthermore, as shown in FIG. 8C, a crank mechanism 58 may be used in addition to the constitution including the band and the reel.

In the present example, the piston displacement restricting unit has the band 56 as a band-like body having an end portion connected to the piston and the reel 57 as a band-like body windup portion that changes a length of the band 56 to be played out. Furthermore, the above-mentioned changing unit allows the reel 57 to change the length of the band 56 to be played out, thereby changing the displacement amount of the piston 40.

Figure 9:
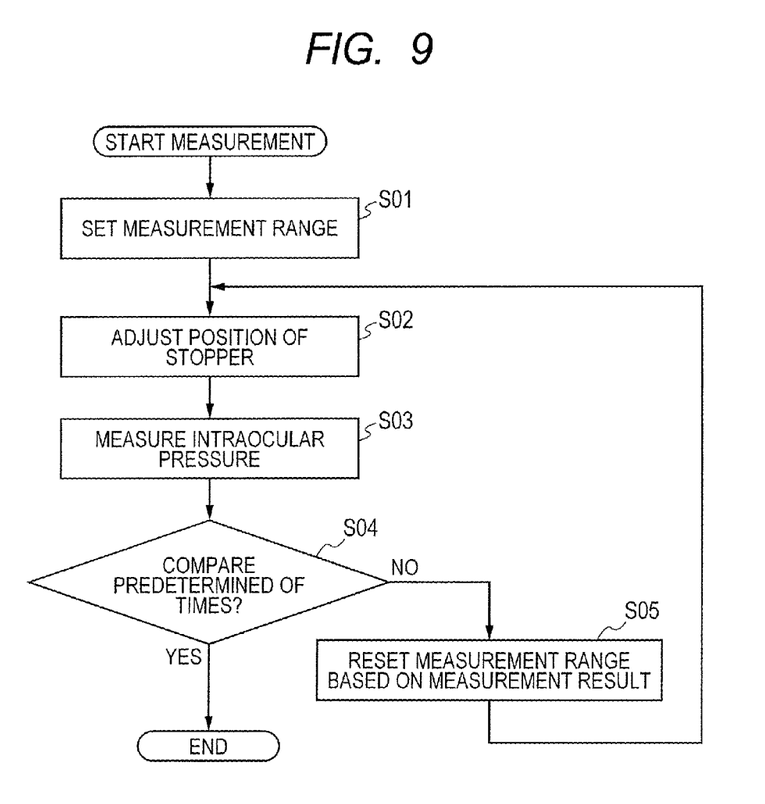
FIG. 9 is a chart showing a measurement flow in the embodiment shown in FIG. 1.

One example of a measurement flow of the present invention will be described with reference to a flowchart of FIG. 9. In step S01, the system control portion 100 reads the measurement range stored in the memory portion 103, and sets the measurement range (the measurement range of the intraocular pressure values). In step S02, the system control portion 100 drives the motor 111 that adjusts the position of the stopper on the basis of the measurement range set by the system control portion, so that the stopper is disposed at a position where the intraocular pressure value of an upper limit of the set measurement range can be measured and the movement of the piston by the inertia is decreased. In step S03, the system control portion 100 drives the rotary solenoid 42, so that the piston 40 ejects the pressurized air from the nozzle 22 toward the cornea Ec of the eye E to be inspected. The pressure signal detected by the pressure sensor 45 of the air chamber 23 and a light receiving signal from the light receiving element 34 are stored in the memory portion 103 by the system control portion 100. The system control portion 100 calculates the intraocular pressure value from a peak value of the light receiving signal and the pressure signal at this time on the basis of information stored in the memory portion 103. The system control portion 100 displays the calculated intraocular pressure value in the monitor 106. In step S04, it is judged whether the number of measurement times reaches a predetermined number of the times. In step S05, to reduce the air to be blown as much as possible in the next measurement, the system control portion resets the measurement range of the next time based on the measured intraocular pressure value, i.e., the measurement result of the previous time, and the system control portion shifts to the adjustment of the position of the stopper.

The constitution of the apparatus in the present embodiment has been described above.

Other Embodiment

Furthermore, the present invention is realized also by executing the following processing. That is, in the processing, software (a program) that realizes the function of the above-mentioned embodiment is supplied to a system or an apparatus via a network or various storage mediums, and the system or a computer (or a CPU, an MPU or the like) of the apparatus reads and executes the program.

While the present invention has been described with reference to exemplary embodiments, it is to be understood that the invention is not limited to the disclosed exemplary embodiments. The scope the following claims is to be accorded the broadest interpretation so as to encompass all such modifications and equivalent structures and functions.

This application claims the benefit of Japanese Patent Application No. 2013-096791, filed Apr. 17, 2013, which is hereby incorporated by reference herein in its entirety.

What is claimed is:

1. A non-contact tonometer comprising:
a piston;
a driving unit which is connected to the piston so as to drive the piston;
a fluid ejection unit configured to blow air pressurized by driving the piston, which is disposed in a cylinder, toward a cornea of an eye to be inspected;
an intraocular pressure measuring unit configured to measure an intraocular pressure of the eye by optically detecting a deformed state of the cornea; and
a stopper that restricts a displacement range of the piston, wherein the restricted displacement range of the piston is changeable according to a measurement range of the intraocular pressure.

2. The non-contact tonometer according to claim 1, wherein the stopper is disposed in a movable range of at least one of the piston and the driving unit.

3. The non-contact tonometer according to claim 1, wherein the restricted displacement range of the piston is changed based on a measurement range of intraocular pressure values that are to be measurable.

4. The non-contact tonometer according to claim 3, wherein the measurement range of the intraocular pressure values that are to be measurable is changed based on a measurement result of a previous time.

5. The non-contact tonometer according to claim 1, wherein the stopper can be moved in a direction of movement of the piston so as to adjust a position where the stopper comes in contact with a driving lever of the driving unit.

6. The non-contact tonometer according to claim 1, wherein the driving unit comprises a rotary solenoid and a driving lever,
wherein the fluid ejection unit comprises the cylinder, a transfer tube, and an air chamber, and
wherein the intraocular pressure measurement unit comprises a measuring light source and a light receiving element.

7. The non-contact tonometer according to claim 1, wherein the driving unit comprises a solenoid,
wherein the fluid ejection unit comprises the cylinder, and
wherein the intraocular pressure measurement unit comprises a light source.

8. A non-contact tonometer comprising:
a piston;
a driving unit which is connected to the piston so as to drive the piston;
a fluid ejection unit configured to blow air pressurized by driving the piston, which is disposed in a cylinder, toward a cornea of an eye to be inspected;
an intraocular pressure measuring unit configured to measure an intraocular pressure of the eye by optically detecting a deformed state of the cornea; and
a piston displacement restricting unit which includes (1) a band having an end portion connected to the piston and (2) a windup portion that changes a length of the band to be played out so as to restrict a displacement range of the piston.

9. A non-contact tonometer comprising:
a piston disposed in a cylinder, wherein an intraocular pressure is measured by (1) blowing air pressurized by driving the piston in the cylinder toward a cornea of an eye to be inspected, and (2) detecting a deformed state of the cornea of the eye to be inspected; and
a stopper that restricts a displacement range of the piston; wherein the restricted displacement range of the piston can be changed according to a measurement range of the intraocular pressure.

* * * * *